United States Patent [19]

Sheahan

[11] Patent Number: 5,143,568
[45] Date of Patent: Sep. 1, 1992

[54] METHOD FOR LEAK DETECTION AND NON-DESTRUCTIVE QUALITY CONTROL TESTING FOR ROOFING SEAMS

[75] Inventor: James P. Sheahan, Midland, Mich.
[73] Assignee: J.P. Sheahan & Associates, Midland, Mich.
[21] Appl. No.: 426,213
[22] Filed: Oct. 25, 1989
[51] Int. Cl.⁵ .............................. B32B 31/00
[52] U.S. Cl. ..................... 156/64; 73/40.7; 73/40.5 R; 52/173 R
[58] Field of Search .......... 73/40.5 R, 40.7; 156/64, 71; 52/173 R

[56] References Cited

U.S. PATENT DOCUMENTS 4,723,109  2/1988  Sheahan ............... 52/173 R
4,748,847  6/1988  Sheahan ............... 73/40.7

FOREIGN PATENT DOCUMENTS 1179472  12/1984  Canada ................ 156/71

*Primary Examiner*—David A. Simmons
*Assistant Examiner*—Robert Barker
*Attorney, Agent, or Firm*—Robert L. McKellar

[57] ABSTRACT

There is disclosed a method of non-destructive quality control testing of seams in roof membranes. The test comprises the use of a double seam concept which forms a pressurizable void, which indicates the degree and extent of bonding of the seams. The test is corralatable to T-pull testing normally used in the laboratory for such testing but has the advantage of being capable of being used on the construction site.

27 Claims, 2 Drawing Sheets

METHOD FOR LEAK DETECTION AND NON-DESTRUCTIVE QUALITY CONTROL TESTING FOR ROOFING SEAMS

BACKGROUND OF THE INVENTION

This invention deals with a method of quality control testing and leak detection for roofing seams. The method is non-destructive and can be applied to already existing old roof seams, newly installed roof seams, or seams in factory manufactured roofing materials before they are installed in a roofing system.

Large industrial and commercial buildings quite typically have flat or near flat roof surfaces. These roof surfaces generally are multi-layered, that is, they generally have in combination a roof supporting structure which is surmounted by a deck, and various layers of water impermeable membranes, thermal insulation and a ballast layer to assist in holding the entire roof from being blown away.

Single ply roof membranes of elastomeric or thermoplastic materials are seamed by bonding the roof materials together using sheets of varying widths and lengths to form an integrated membrane for covering the roof surface. The quality and integrity of the membrane is dependent on the quality of the seams and one of the largest problems in producing such large flat roofs is the quality of the bonds in the seams that are provided in the single ply membranes that are used as the water impermeable layers in such roofs. This problem is of continual concern to the industry because the leakage problem is so severe. It causes degradation of other roof components and such leaks are difficult to locate.

The weatherable and essentially inert materials that are used for the single ply roofing materials are known to have multiple problems with bonding to themselves and to each other, and consequently, the seams created from these materials are an unknown entity. For example, practitioners experience false welds or bonds due to moisture on the surface of the material. Welding guns may be cold when they were thought to be heat sealing. Marks used for stopping and starting the bonding may have been missed and a problem with the use of reinforcement, which boils off and blisters the polymeric materials and ruptures the bonds are all common faults in the application of roofs.

The quality of a seam once it is manufactured cannot be determined in a non-destructive fashion. On visual examination, all seams look good if just the last outside 1/16 inch of the nominally 1½ inch wide seam is sealed.

The use of mechanical probing has been carried out on the this very thin line of bond at the very extreme edge of the seam, fortunately, it is the easiest part to seam, but even knowing the extent of bonding of this leading edge, does not give the true picture of the area or quality of the bond of the entire seam.

Caulk is sometimes used for protecting such seams and in a number of cases becomes the only bonded and sealed portion of such seams but is not considered to be a very effective solution to a fully bonded seam area.

Laboratory testing has included such practices as ultrasound, pulse-echo techniques, infra-red imagery and so forth, but these have not proven adaptable for field use.

The more progressive commercial roofing companies tend to use a T-peel test to check the quality of the seams during construction or when a problem roof demands some attention. This T-peel test is a very simple stress/strain test wherein two sides of a lapped roofing material are put into the vertical holding jigs of a tensile testing machine and pulled at an angle of 180° from each other, and at a specific rate. Such machines are manufactured by the Instron Corporation and are hence sometimes called the "Instron test". The machines are designed such that the loads required to pull the laps apart are directly recorded along with the width of the sample so that the load/area normally reported in units of pound/inch may be observed. Using this type of test, the range of strength for those seams that are bonded together is about 4 to 8 pounds per inch of width, and fused materials, i.e. those that are essentially melted together, range to about 20 to 40 pounds per inch of width. This test has proven to be ineffective and insensitive to improperly prepared surfaces. Obviously, a further difficulty with this type of quality control testing is that it is a destructive test, taking some time, usually in a site away from the construction location. Also, it causes damage to the roof at several places along each seam and makes it very difficult for the contractor to repair certain areas of the roof as very often the roof surface is not clean.

Further, there is an ongoing disagreement among those in the industry as to whether the test truly represents the quality of the seams because only small portions of the seams are being tested in width and length. The small samples tested are supposed to represent the many miles of seams on a roof, but is believed by the more progressive commercial roofers that such is not the case. Measuring the full area of the bonding of seams is a valuable asset in addition to being able to measure the strength of the bond which is a measure of the quality of the seam, and thus, the instant invention is timely.

Since applicant was not able to locate any patents or publications in the prior art regarding the instant invention, it is believed by the applicant that the method is new and novel.

SUMMARY OF THE INVENTION

The present invention therefore deals with solutions to the problems of quality control testing of the seams of a single ply roofing assembly to quickly and accurately determine if the seams have the strength to hold up under normal weathering circumstances. It also applys to a novel leak detection method for such seams, both methods being non-destructive to the roof seam.

The instant invention in one particular therefore comprises a method of non-destructive testing comprising: (A) overlapping at least two pieces of roofing material in preparation for creating a seam; (B) bonding the overlapped roofing materials at approximately the leading edge of the bottommost roofing material; (C) bonding the overlapped roofing materials at approximately the leading edge of the uppermost roofing material approximately parallel to the bond created in (B), thereby creating a seam; (D) bonding the overlapped roofing materials at least at each of the terminal ends of the seam created, thereby forming an unbonded void area between the bond created in (B), the bond created in (C), the bonds created in (D), and the overlapped roofing materials; (E) providing a gas injection means at any point along the seam length to be tested; (F) injecting a gas into the unbonded void area to create a known pressure within the unbonded void area; (G) determining the bond area and the bond strength for the bonded seams.

The instant invention also comprises a method for testing factory manufactured double seamed roofing material and that method is a method of non-destructive testing comprising: (A) providing a double seamed overlapped roofing material; (B) bonding the double seamed overlapped roofing materials at least at each of the terminal ends of the seam created, thereby forming an unbonded void area between the bonds provided by (A), the bond created in (B), and the overlapped roofing materials; (C) providing a gas injection means at any point along the seam length to be tested; (D) injecting a gas into the unbonded void area to create a known pressure within the unbonded void area; (E) determining the bond area and bond strength for the bonded seams.

In another particular segment of this invention the method comprises a system of non-destructive testing in seamed roofing, wherein a small spot or short length of roofing seam can be tested without testing the entire length of the seam. The method comprising (A) overlapping at least two pieces of roofing material in preparation for creating a seam; (B) bonding the overlapped roofing materials at approximately the leading edge of the bottommost roofing material, (C) bonding the overlapped roofing materials at approximately the leading edge of the uppermost roofing material approximately parallel to the bond created in (B), thereby creating a seam; (D) bonding the overlapped roofing materials at least at each of the terminal ends of the seam created, thereby forming an unbonded void area between the bond created in (B), the bond created in (C), the bonds created in (D), and the overlapped roofing materials; (E) providing a gas injection means at any point along the seam length to be tested; (F) providing a weighted air barrier on a seam length to be tested; (G) injecting a gas into the unbonded void area to create a known pressure within the unbonded void area; (H) determining the bond area and the bond strength for the bonded seams.

Yet another aspect of this invention is a quality control check for commercial, factory manufactured, seamed roofing material, before the material is used in a roof system, wherein the method is a non-destructive testing method comprising: (A) providing a double seamed overlapped roofing material; (B) bonding the double seamed overlapped roofing materials at least at each of the terminal ends of the seam created, thereby forming an unbonded void area between the bonds provided by (A), the bond created in (B), and the overlapped roofing materials; (C) providing a gas injection means at any point along the seam length to be tested; (D) providing a weighted air barrier on the seam length to be tested; (E) injecting a gas into the unbonded void area to create a known pressure within the unbonded void area; (F) determining the bond area and bond strength for the bonded seams.

Still another aspect of this invention is a method of testing the strength of and obtaining leak detection of single seams in roofing membranes.

As indicated, this invention also deals with a simple method of testing single seamed i.e. single bonded roofing materials, whether or not the seams are manufactured on the roof surface, or whether they are pre-manufactured off the roof. Such a method uses in part, the method described above for determining leaks in spot checks for short lengths of seams utilizing the weighted air barrier technique. With reference to FIG. 4, there is shown a double seam roof material i.e. a double bonded roof material of this invention, wherein the material is bonded at 5 and also at 6. A single seam roof material would be similar, except the bond at 5 would not exist, the bottommost layer simply being tacked or nailed onto the deck surface and the topmost layer being overlapped and bonded only at 6. In FIG. 4, assuming a single bonded seam, it is imperative that the weighted air barrier be modified at L such that L also contacts and compresses the surface of the topmost layer thereby creating an air barrier between L and the iron bars where the laborer has placed his feet, the bond 6 acting as the fourth barrier edge. It should be noted that this weighted air barrier has been illustrated using the weight of a workman to hold down the weighted air barrier, but it is within the scope of this invention, and contemplated by the inventor herein that any manner of weight can be used, for example, bricks, blocks, additional iron, weighted wheelbarrows, and the like.

Still further, this invention comprises a method of leak detection in roof systems comprising (A) overlapping at least two pieces of roofing material in preparation for creating a seam; (B) bonding the overlapped roofing materials at approximately the leading edge of the bottommost roofing material; (C) bonding the overlapped roofing materials at approximately the leading edge of the uppermost roofing material approximately parallel to the bond created in (B), thereby creating a seam; (D) bonding the overlapped roofing materials at least at each of the terminal ends of the seam created, thereby forming an unbonded void area between the bond created in (B), the bond created in (C), the bonds created in (D), and the overlapped roofing materials; (E) providing a gas injection means at any point along the seam length to be tested; (F) injecting a detectable gas into the unbonded void area to create a pressure within the unbonded void area; (G) determining the points of leakage of the detectable gas along the seam.

Finally, this invention deals with a method of detecting leaks in roofing material seams, before the roofing material in used in a roof system, the method comprising (A) providing a seamed overlapped roofing material; (B) bonding the double seamed overlapped roofing materials at least at each of the terminal ends of the seam created thereby forming an unbonded void area between the bonds provided by (A), the bond created in (B), and the overlapped roofing materials; (C) providing a gas injection means at any point along the seam length to be tested; (D) injecting a detectable gas into the unbonded void area to create a pressure within the unbonded void area; (E) determining the points of leakage of the detectable gas along the seam.

DESCRIPTION OF THE PREFERRED EMBODIMENTS

Figure 1:
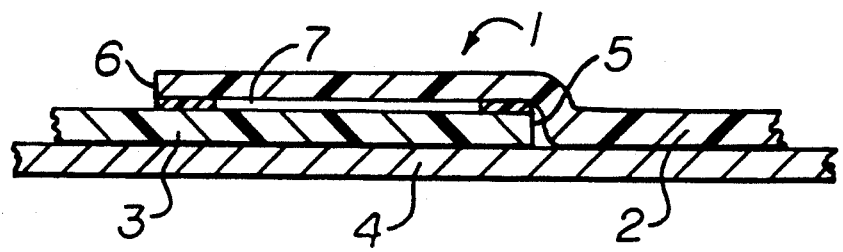
FIG. 1 is a sectional side view of a double bonded overlapped seam i.e. double seam, created by the overlapping of two adjacent pieces of single ply roofing material.

Referring now to the drawings in which like-numbers indicate like-parts or pieces, there is shown in FIG. 1, a sectional side view of an overlapped seam 1 created by the overlapping of two adjacent pieces of single ply roofing material, the bottommost layer being illustrated as 3 and the uppermost layer being illustrated as 2. The materials of construction may be the same kind of materials or they may be different from each other.

In the instant inventive method, when the roof is being newly installed, the preparations for the quality control check of the seams begins with the creation of the seams, it being understood for purposes of this disclosure that only one bond seams are normally used in single ply roofing and that the creation of the second bonded area is not normally required in single ply roofing, nor is it necessarily denoted as a seam, and that the creation of the second bonded area is for the purpose of carrying out one aspect of the method of this invention. Throughout this specification, it should be noted that the bonded areas are designated as "seams", irrespective of their eventual use in this inventive method.

Thus, the bottommost layer 3 is laid on the roof structure 4 and the uppermost layer 2 is lapped over the bottommost layer 3. This overlap usually consists of an overlap in the range of 4 to 8 inches depending on the type of material used and the type of roof being constructed. The leading edge 5 of the bottommost layer 3 is either glued or fused, depending on the type of single ply material being used to the uppermost layer 2. Then, the uppermost layer 2 is laid down on the bottommost layer 3 and bonded at the leading edge 6 of the uppermost layer 2. By this bonding method, there is created two, essentially parallel bonded strips which constitute seams (i.e. a double seam), and an area 7 between the two seams which is non-bonded i.e. a void area. A further means of providing an unbonded surface at the indicated area 7, is to construct the seam with a non-fusible or non-glueable interlayer between the two layers of single ply materials as the roof is being assembled. This more or less guarantees a certain amount of non-bonded area in the seam. In typical roofing assemblys, the roof coverings are also bonded around the outside edges of the roof, thereby creating long seams also having bonds at each of their ends.

After the double seam is fully bonded, it is ready for testing. This inventive method can be used on almost any length of seam, from several inches to several hundred feet in length, and it can be used for testing irregular shaped seams, such as patches, corner assemblies, edges, and the like. Such irregular shapes do not have to be double bonded however, as it is obvious that they would generally have single seams about their outside edges, for example, it is common to use saucer shaped patches made of single ply roofing material to cover holddown devices on roof surfaces to prevent leaking through or around such devices. These saucer shaped patches are laid down over the holddown devices and their outer edges bonded to the existing single ply roofing material. For purposes of this invention, an entire seam length can be tested at one time. In another embodiment of this invention, it will be observed that short sections of essentially linear seams can also be tested by the use of the methods of this invention including the use of a weighted air barrier. For roofing materials that contain pre-manufactured single seams, or for roofing materials that are already in place, for example, newly created single seams, the use of a weighted air barrier in the form of a jig which has been made out of heavy angle iron can be used by laying it flat on the surface of the single ply, single seamed materials, so as to create a predetermined area of the seam thus forming an air barrier encompassing a predetermined length and width of the seam.

The instant invention is not limited to the use of the weighted air barrier on single seamed materials. When one wishes to check short segments of double bonded seams, a weighted air barrier ca also be used. The weighted air barrier approach has practical utility as the barrier is transportable is essentially light weight, can be weighted by the body weight of the workman testing the seam, or it can be weighted by cement blocks, iron plates, or the like, it being understood that the configuration of the barrier is not critical and that it can be rectangular, square, circular, or the like in configuration. What is critical is that an air barrier is formed around the entire seam to be tested such that the gas used in the test will not escape the seam except at a failure point in the seam, it being understood that the double bonded seams do not require a three sided barrier, whereas a single bonded seam would require the barrier to have three sides which contact and compress the single ply roofing material in order to form an air barrier around the seam. Thus, in single seam roof membranes, the angle iron would need to have three sides contacting and compressing the surface of the membrane in order to cause the existing seam to be the fourth side and thus enable one to create a pressure against the seam.

Figure 2:
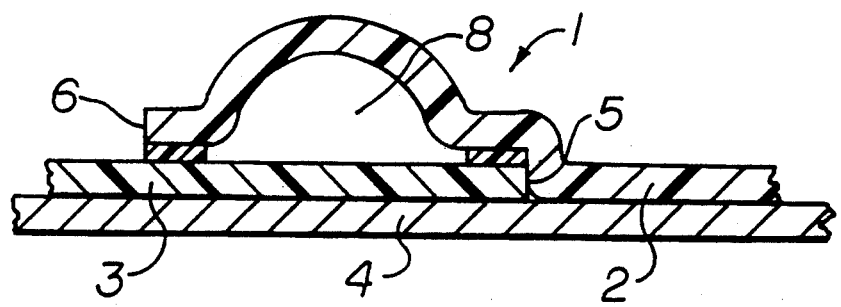
FIG. 2 is a sectional side view of the overlapped seam as shown in FIG. 1, except this view shows the seam after the injection of a gas. In the practical application of the methods of this invention, the bottom layer 3 would also be hooped or rounded to create a bicycle tire effect, the amount of hoop or roundness depending on the degree of adhesion of the bottom layer to the under substrate; the amount of gas that has been injected, and the degree of bonding of the top layer to to the bottom layer of the membrane it being further understood that the layers 2 and 3 would also not remain on the roof substrate at this point owing to the lifting effect provided by layer 3 when fully pressurized into its bicycle configuration.
Figure 3:
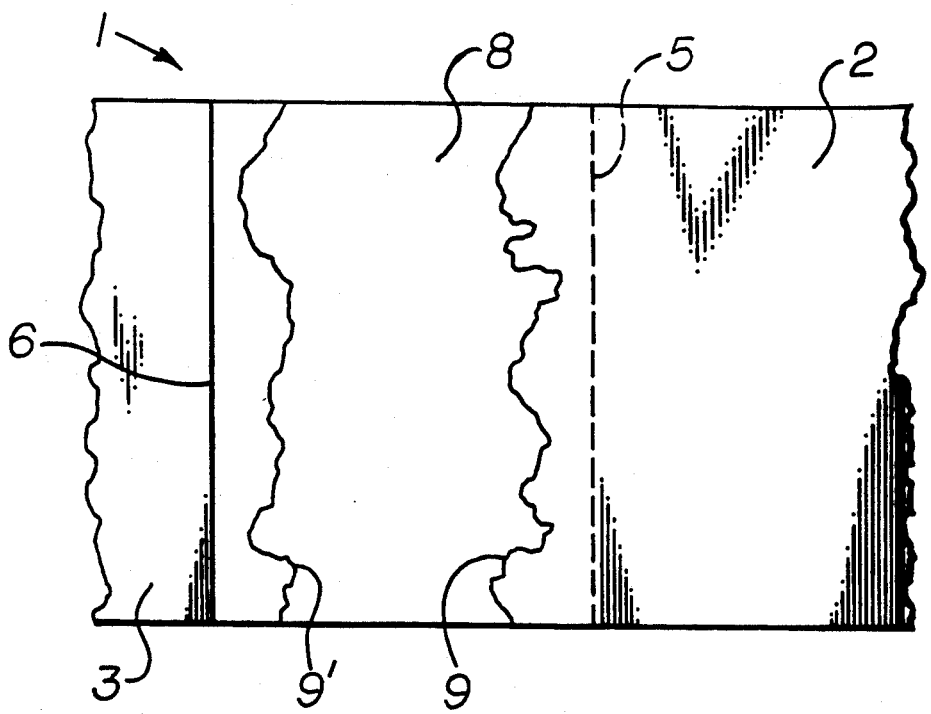
FIG. 3 is a full top view of a section of single ply roofing material having the seam of FIG. 2, which has been pressurized by the injection of a gas to show the normal irregularity of the seam width when first bonded.
Figure 4:
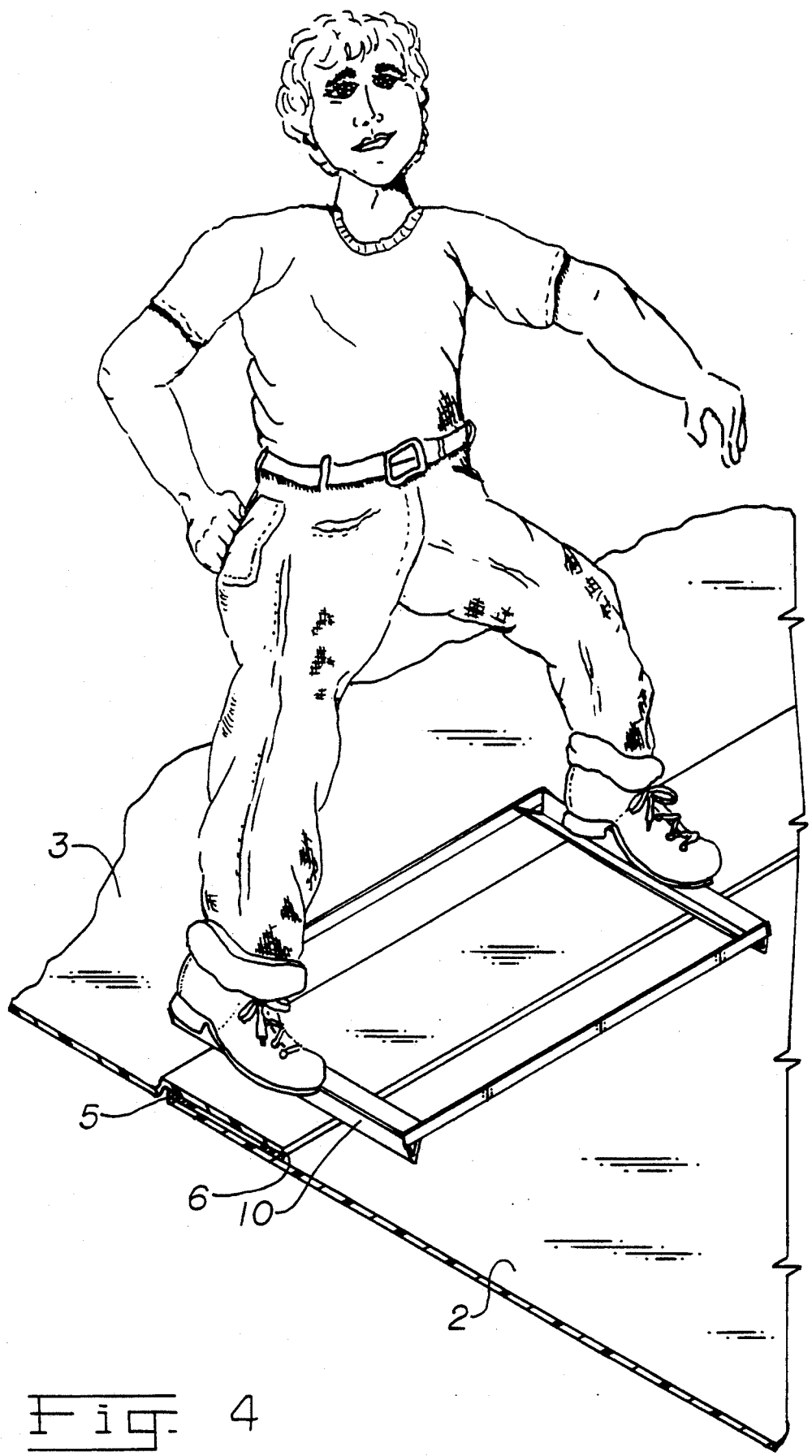

The seam is now ready to be pressurized and tested. For this purpose, a means is provided for injecting air into the unbonded void area between the seams. Useful as a gas injection means can be a small valve, such as a basketball inflating valve, which can be attached to a gas source, such as compressed air, or hand pumped air. The air is injected into the void and the pressure created by the forced air forms a cylindrical or elliptical shape 8 out of the materials that are seamed, and trapped by the air barriers, such as that shown in FIG. 2. If the conventional overlap widths and seam widths are adhered to, then the void will have the approximate configuration of a bicycle tire. The shape of the seam created by pressurizing of the void can be readily observed and as shown in FIG. 3, gives an irregular pattern 9 and 9' against both sides of the formed cylindrical or irregular shape 8. The shape thus created, can be traced by a colored pencil or chalk on the upper surface of the roofing material to show the width and the outline of the bonding of each side of the seams. By adjusting the pressure within the trapped area, there is created a tensile stress on the walls of the cylindrical shape. By examining the interface between the bottom and top materials it can be seen that essentially the "T" peel arrangement is developed in situ. By simple mathematical expression, the pressure within the system can be converted to loads measured in pounds per inch of width. The quality control test can be run to a level of about 70 to 80 percent of the desired testing strength and indicated as being acceptable or not acceptable. If not acceptable, the roof can be repaired immediately at that point.

An expression to convert the loads to familar units of pounds per inch of width is found in the "Handbook of Engineering Fundamentals", Eshbach, O.V. and Souders. M., 3rd edition, John Wiley & Sons, New York, page 541, and takes the following form:

The second formula for cylinders refers to the load in the transverse direction. It can be seen that the load in pounds per square inch is equal to the pressure in psi times the diameter in inches divided by a constant of 4 and divided by the thickness of the material being tested. By deleting the thickness of the material, that is, taking the pressure results times the thickness in inches, the units are transferred to pounds per inch of width. Therefore the simplest formula would be: the load in pounds per inch of width is directly proportional to the pressure times the diameter divided by 4.

Thus, for example if the material has the capability of developing a "T" strength of 40 pounds per inch of width and is designated to test passing of 30 pounds per inch of width, using a diameter of one inch, which is equal to the width of the unbonded space between the two seamed areas the pressure would be as high 120 psi. As the diameter increases with rupturing of the bond, the stress in pounds per inch goes up directly and proportionally.

By way of example, tests were conducted on a known commercial roofing membrane, Durolast. The tests were run on field and factory seams to establish the amount of T-pull necessary to break the membrane weld. To confirm the test results, T-pull tests with established weight settings were used to establish standard values of the strength of the seams.

Tests on the DuroLast seams with air pressure were conducted wherein the air pockets were approximately 1¼ inches wide using field and factory seams to close in the air pockets. The amount of air pressure necessary to T-pull the factory seam varied between 22.5 pounds/inch and 30 pounds/inch. To check the results of the tests, a weight test was used. Metal grips were used to hold each end of the seam, and a scale was joined to one of the metal grips. A weight was joined to the other metal grip, and the weight was allowed to drop and pull in a downward vertical motion. The hanging weight T-pull took between 45 seconds and 2 minutes on several pulls to break the factory weld. The factory seam weld broke in an average of 27.5 pounds/inch, and the same test showed that the field welds broke at an average of 30.5 pounds/inch, indicating that the inventive testing method corresponded quite well with the in-laboratory test.

A second testing method was used designated for purposes of this disclosure, the "angle iron closed track test".

An angle iron closed track measuring 6 inches by 24 inches was designed for further use in testing of T-pull seams in the field. This allowed an inspector to test any seams at random on a finished roof system. This closed track can be used in making its own air pockets at any distance desired by the field inspector within the confines of less than one inch to 24 inches. By applying pressure from an air pressure tank, the pressure can be set knowing the area of air pocket made. The pressure can then be set to the requirements of testing the seams without breaking them or finding out that the seam is weak. The amount of pressure applied by the device is dependent on the weight applied. A one hundred eighty pound man using it can use approximately 6 to 8 pounds of pressure. Field seams constructed on elastomeric material, using an adhesive to make the seams, required less than 4 pounds of pressure to break the seam. In order to get a more balloon-like shape to achieve a T-pull test within the track area, the track has a tendency to pull the membrane into the area of the truck to achieve it's needed shape. The material does not have enough elasticity to form a balloon shape without pulling the membrane into the track area. A slight downward angle was bent in the 24 inch side of the track. This allowed additional pressure to be applied to hold the membrane airtight. Membranes of both elastomeric and plastic were tested, the elastomeric membrane being tested in it's field bonds; the plastic membrane being tested on it's factory and field bonds.

That which is claimed is:

1. A method of non-destructive testing comprising:
   (A) overlapping at least two pieces of roofing material in preparation for creating a seam wherein the roofing material is selected from a group consisting of (a) elastomeric roofing materials and, (b) thermoplastic roofing materials;
   (B) bonding the overlapped roofing materials at approximately the leading edge of the bottommost roofing material;
   (C) bonding the overlapped roofing materials at approximately the leading edge of the uppermost roofing material approximately parallel to the bond created in (B), thereby creating a seam;
   (D) bonding the overlapped roofing materials at least at each of the terminal ends of the seam created, thereby forming an unbonded void area between the bond created in (B), the bond created in (C), the bonds created in (D), and the overlapped roofing materials;
   (E) providing a gas injection means at any point along the seam length to be tested;
   (F) injecting a gas into the unbonded void area to create a known pressure within the unbonded void area;
   (G) determining the bond area and the bond strength for the bonded seams.

2. A method as claimed in claim 1 wherein the seam is linear.

3. A method as claimed in claim 1 wherein the seam is non-linear.

4. A method as claimed in claim 1 wherein the seam is a patch.

5. A method as claimed in claim 4 wherein the patch is rectangular.

6. A method as claimed in claim 4 wherein the patch is square.

7. A method of non-destructive testing comprising:
   (A) providing a double seamed overlapped roofing material wherein the roofing material is selected from a group consisting of (a) elastomeric roofing materials and (b) thermoplastic roofing materials;
   (B) bonding the double seamed overlapped roofing materials at least at each of the terminal ends of the seam created, thereby forming an unbonded void area between the bonds provided by (A), the bond created in (B), and the overlapped roofing materials;
(C) providing a gas injection means at any point along the seam length to be tested;
(D) injecting a gas into the unbonded void area to create a known pressure within the unbonded void area;
(E) determining the bond area and bond strength for the bonded seams.

8. A method of non-destructive testing comprising:
(A) overlapping at least two pieces of roofing material in preparation for creating a seam wherein the roofing material is selected from the group consisting of (a) elastomeric roofing materials and (b) thermoplastic roofing materials;
(B) bonding the overlapped roofing materials at approximately the leading edge of the bottommost roofing material;
(C) bonding the overlapped roofing materials at approximately the leading edge of the uppermost roofing material approximately parallel to the bond created in (B), thereby creating a seam;
(D) bonding the overlapped roofing materials at least at each of the terminal ends of the seam created, thereby forming an unbonded void area between the bond created in (B), the bond created in (C), the bonds created in (D), and the overlapped roofing materials;
(E) providing a gas injection means at any point along the seam length to be tested;
(F) providing a weighted air barrier around a seam length to be tested;
(G) injecting a gas into the unbonded void area to create a known pressure within the unbonded void area;
(H) determining the bond area and the bond strength for the bonded seams.

9. A method of non-destructive testing comprising:
(A) providing a double seamed overlapping roofing material wherein the roofing material is selected from a group consisting of (a) elastomeric roofing materials and (b) thermoplastic roofing materials;
(B) bonding the double seamed overlapped roofing materials at least at each of the terminal ends of the seam created, thereby forming an unbonded void area between the bonds provided by (A), the bond created in (B), and the overlapped roofing materials;
(C) providing a gas injection means at any point along the seam length to be tested;
(D) providing a weighted air barrier around a seam length to be tested;
(E) injecting a gas into the unbonded void area to create a known pressure within the unbonded void area;
(F) determining the bond area and bond strength for the bonded seams.

10. A method of leak detection in a roof system comprising:
(A) overlapping at least two pieces of roofing material in preparation for creating a seam wherein the roofing material is selected from a group consisting of (a) elastomeric roofing materials and (b) thermoplastic roofing materials;
(B) bonding the overlapped roofing materials at approximately the leading edge of the bottommost roofing material;
(C) bonding the overlapped roofing materials at approximately the leading edge of the uppermost roofing material approximately parallel to the bond created in (B), thereby creating a seam;
(D) bonding the overlapped roofing materials at least at each of the terminal ends of the seam created, thereby forming an unbonded void area between the bond created in (B), the bond created in (C), the bonds created in (D), and the overlapped roofing materials;
(E) providing a gas injection means at any point along the seam length to be tested;
(F) injecting a tracer gas into the unbonded void area to create a pressure within the unbonded void area;
(G) determining the points of leakage of the tracer gas along the seam.

11. A method of leak detection in a roof system comprising:
(A) providing a double seamed overlapped roofing material wherein the roofing material is selected from a group consisting of (a) elastomeric roofing materials and (b) thermoplastic roofing materials;
(B) bonding the double seamed overlapped roofing materials at least at each of the terminal ends of the seam created, thereby forming an unbonded void area between the bonds provided by (A), the bond created in (B), and the overlapped roofing materials;
(C) providing a gas injection means at any point along the seam length to be tested;
(D) injecting a tracer gas into the unbonded void area to create a pressure within the unbonded void area;
(E) determining the points of leakage of the tracer gas along the seam.

12. A method of leak detection in a roof seam comprising:
(A) overlapping at least two pieces of roofing material in preparation for creating a seam wherein the roofing material is selected from a group consisting of (a) elastomeric roofing materials and (b) thermoplastic roofing materials;
(B) bonding the overlapped roofing materials at approximately the leading edge of the bottommost roofing material;
(C) bonding the overlapped roofing materials at approximately the leading edge of the uppermost roofing material approximately parallel to the bond created in (B), thereby creating a seam;
(D) bonding the overlapped roofing materials at least each of the terminal ends of the seam created, thereby forming an unbonded void area between the bond created in (B), the bond created in (C), the bonds created in (D), and the overlapped roofing materials;
(E) providing a gas injection means at any point along the seam length to be tested;
(F) providing a weighted air barrier on the seam length to be tested;
(G) injecting a tracer gas into the unbonded void area to create a pressure within the unbonded void area;
(H) determining the points of leakage of the tracer gas along the seam.

13. A method of leak detection in a roof seam comprising:
(A) providing a double seamed overlapped roofing material wherein the roofing material is selected from a group consisting of (a) elastomeric roofing materials and (b) thermoplastic roofing materials;

(B) bonding the double seamed overlapped roofing materials at least at each of the terminal ends of the seam created, thereby forming an unbonded void area between the bonds provided by (A), the bond created in (B), and the overlapped roofing materials;

(C) providing a gas injection means at any point along the seam length to be tested;

(D) providing a weighted air barrier on the seam length to be tested;

(E) injecting a tracer gas into the unbonded void area to create a pressure within the unbonded void area;

(F) determining the points of leakage of tracer gas along the seam.

14. A method of leak detection in a roof seam, the method consisting essentially of (A) injecting a tracer gas into an open area of a seam in a double seamed roof membrane wherein the membrane is selected from a group consisting of (a) elastomeric roofing materials and (b) thermoplastic roofing materials;

(B) detecting the injected tracer gas at the seam with a detector that is detection sensitive to the tracer gas to detect any escape of the tracer gas from the seam.

15. A method as claimed in claim 14 wherein the tracer gas is a halogenated hydrocarbon.

16. A method as claimed in claim 15 wherein the halogenated hydrocarbon is a fluorinated hydrocarbon.

17. A method as claimed in claim 16 wherein the halogenated hydrocarbon is dichlorodifluoromethane.

18. A method of leak detection comprising:

(A) providing a single seamed overlapped roofing material wherein the roofing material is selected from a group consisting of (a) elastomeric roofing materials and (b) thermoplastic roofing materials;

(B) providing a weighted air barrier around a seam length to be tested;

(C) providing a gas injection means at any point along the seam length to be tested;

(D) injecting a gas into the seam to create a pressure within any unbonded void area;

(E) determining the points of leakage along the seam.

19. A method of leak detection in a roof seam comprising:

(A) overlapping at least two pieces of roofing material in preparation for creating a seam wherein the roofing material is selected from a group consisting of (a) elastomeric roofing materials and (b) thermoplastic roofing materials;

(B) bonding the overlapped roofing materials at approximately the leading edge of the bottommost roofing material;

(C) bonding the overlapped roofing materials at least at each of the terminal ends of the seam created;

(D) providing a weighted air barrier on the seam length to be tested;

(E) providing a gas injection means at any point along the seam length to be tested;

(F) injecting a tracer gas into the seam to create a pressure within any unbonded void area;

(G) determining the points of leakage of the tracer gas along the seam.

20. A method of leak detection in a roof seam comprising:

(A) providing a seamed overlapped roofing material wherein the roofing material is selected from a group consisting of (a) elastomeric roofing materials and (b) thermoplastic roofing materials;

(B) bonding the seamed overlapped roofing materials at least at each of the terminal ends of the seam;

(C) providing a weighted air barrier on the seam length to be tested;

(D) providing a gas injection means at any point along the seam length to be tested;

(E) injecting a tracer gas into any unbonded void area to create a pressure within the unbonded void area;

(F) determining the points of leakage of tracer gas along the seam.

21. A method of leak detection comprising:

(A) providing a single seamed roofing material wherein the roofing material is selected from a group consisting of (a) elastomeric roofing materials and (b) thermoplastic roofing materials;

(B) providing a gas injection means at any point in the seam to be tested;

(C) injecting a gas into the seam to create a pressure within any unbonded void area;

(D) determining the points of leakage along the seam.

22. A method as claimed in claim 21 wherein the seam is linear.

23. A method as claimed in claim 21 wherein the seam is non-linear.

24. A method as claimed in claim 21 wherein the seam is a patch.

25. A method as claimed in claim 24 wherein the patch is rectangular.

26. A method as claimed in claim 24 wherein the patch is square.

27. A method as claimed in claim 23 wherein the seam is round.

* * * * *